US008151650B2

(12) United States Patent
Jeppesen et al.

(10) Patent No.: US 8,151,650 B2
(45) Date of Patent: Apr. 10, 2012

(54) TUNING OF MATERIALS TESTING MACHINE

(75) Inventors: Ben Jeppesen, High Wycombe (GB); Paul Hayford, Holmer Green (GB)

(73) Assignee: Illinois Tool Works Inc., Glenview, IL (US)

( * ) Notice: Subject to any disclaimer, the term of this patent is extended or adjusted under 35 U.S.C. 154(b) by 15 days.

(21) Appl. No.: 12/376,742

(22) PCT Filed: Jul. 26, 2007

(86) PCT No.: PCT/IB2007/002143
§ 371 (c)(1),
(2), (4) Date: May 25, 2010

(87) PCT Pub. No.: WO2008/023226
PCT Pub. Date: Feb. 28, 2008

(65) Prior Publication Data
US 2010/0229652 A1    Sep. 16, 2010

(30) Foreign Application Priority Data

Aug. 21, 2006 (GB) .................. 0616590.6
Sep. 15, 2006 (GB) .................. 0618211.7

(51) Int. Cl.
*G01N 3/02* (2006.01)
(52) U.S. Cl. ........................................ 73/856

(58) Field of Classification Search ............. 73/760–860
See application file for complete search history.

(56) References Cited

U.S. PATENT DOCUMENTS

| 4,537,077 | A | * | 8/1985 | Clark et al. ................ 73/665 |
| 4,802,367 | A | * | 2/1989 | Petersen et al. ............ 73/805 |
| 5,090,249 | A | * | 2/1992 | Bielewicz .................. 73/822 |
| 5,511,431 | A | * | 4/1996 | Hinton ...................... 73/806 |
| 5,684,374 | A | * | 11/1997 | Chaffee .................... 318/616 |
| 6,205,863 | B1 | * | 3/2001 | Ishii et al. ................. 73/805 |
| 6,577,975 | B2 | * | 6/2003 | Chiesa ..................... 702/94 |

FOREIGN PATENT DOCUMENTS

| EP | 0 897 110 A2 | 2/1999 |
| EP | 0 897 110 A3 | 2/1999 |
| JP | 07 107766 A | 4/1995 |

OTHER PUBLICATIONS

International Publication No. WO 2008/023226 A2.
International Publication No. WO 2008/023226 A3.
Written Opinion of the International Search Authority.

* cited by examiner

*Primary Examiner* — Max Noori
(74) *Attorney, Agent, or Firm* — Day Pitney LLP

(57) ABSTRACT

In a method of operating a material testing machine for testing a specimen, the machine has an electrically controllable actuator arranged to apply a force to the specimen. The method includes inputting a single adjustable parameter value, calculating all necessary feedback control gains therefrom, and subsequently conducting a test of the specimen.

7 Claims, 2 Drawing Sheets

TUNING OF MATERIALS TESTING MACHINE

Figure 1:
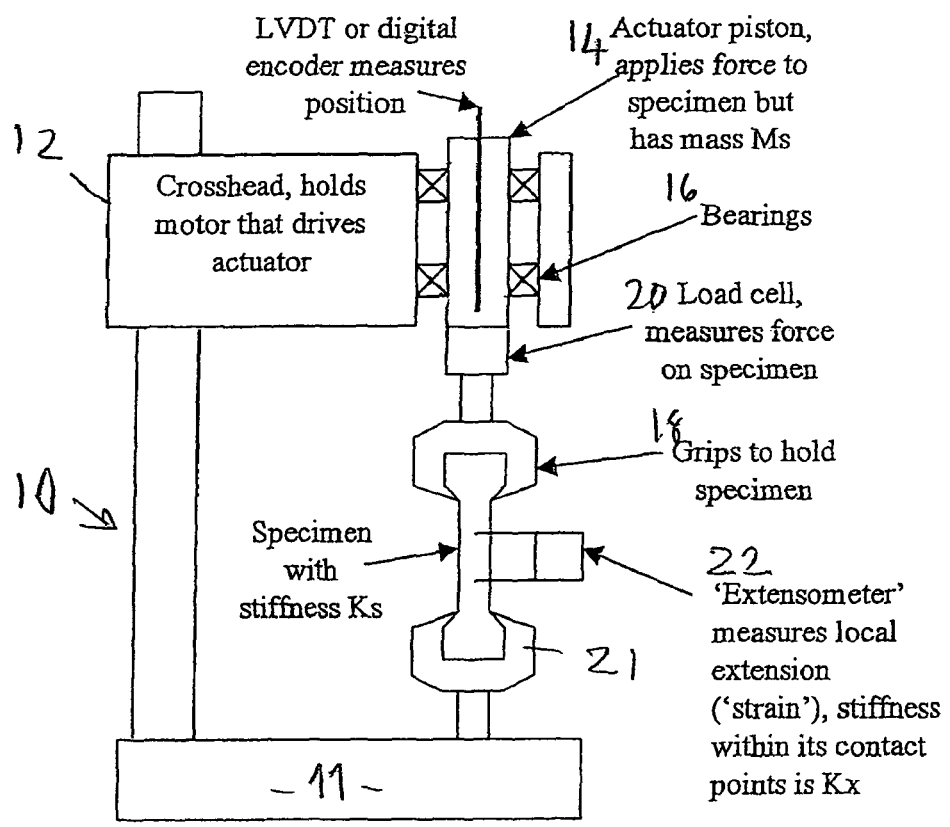

The present invention relates to a materials testing machine and more particularly to a method and apparatus for tuning the machine.

Materials testing machines (also sometimes known as structural test machines) are produced by a number of manufacturers for testing the physical characteristics of material specimens or components. During a test, a particular measured variable must be controlled and must follow a commanded trajectory of values as closely as possible. Some typical variables are:

- position (also sometimes known as displacement or extension)
- load (force on the specimen)
- strain (displacement or extension over a localised part of a specimen).

Examples of actuation technology in such machines are:

- screw-drives driven my electric motors (fine control but limited speed)
- hydraulic actuators (faster response but more complex)
- electro-magnetic shakers (very fast response but limited static load capability)
- linear 3-phase electric motors (fast response and good load capability, may require a lot of electrical power and fast controller).

In all machines, feedback control is used to minimize the error between the commanded variable and current measured value. Most controllers have multiple feedback gains, for example 'P', 'I' and 'D' in a PID controller. There may be further control parameters that need to be set to improve the stability and response, for example velocity feedback, lead-lag compensation or signal filtering. In general, all of these parameters need to be retuned when a new specimen is tested in the machine, because the dynamics of the system are altered substantially by the addition of the specimen. In general, the more dynamic the actuation in the machine, the more need there is for careful tuning of control parameters.

The number of control parameters and the lack of any simple physical relationship between measurable characteristics of the specimen and desirable control parameter values often make the tuning process too complex for a machine operator to accomplish. Instead, control parameters are usually tuned by trained control engineers, based on experience and empirical guidelines. This is expensive and time-consuming, since either the customer using the machine has to invest in highly trained personnel, or the manufacturer has to help tune the machine at the customer's site.

This problem has been recognised for some time and 'auto-tuning' algorithms have been developed to reduce the need for manual tuning. One approach is to automate the empirical guidelines used by control engineers, e.g. an automation of the 'Maximum gain, minimum integral' technique. The resulting control parameters may work well, but several disadvantages remain:

- The process is a 'black box' for the user, with no understanding of what the machine is doing during the tuning process and no simple method of checking that the process has been successful.
- There is still no available physical relationship between the control parameter values and the specimen under test.
- If the control settings are to be stored for reference or set-up purposes, there are many relevant control parameters that must be known to the user and recorded.

Given this state of the art in tuning materials (or structural) test machines, it would clearly be a large improvement for customers and manufacturers of machines if the tuning of a particular specimen required only one parameter. It would be even better if this parameter were a physical characteristic of the specimen under test, which can be measured independently by the user of the machine. This is the invention that is being claimed, which requires only a measure of specimen stiffness to tune all necessary feedback control gains in a materials testing machine.

This is not the first use of 'stiffness' to aid tuning of a materials testing machine. An 'adaptive' control algorithm has already been proposed in our U.S. Pat. No. 5,511,431, which uses stiffness values which are determined automatically during use. However, this algorithm only modifies control gains from initial values that must be tuned empirically, either manually or using an 'autotuning' algorithm that does not use stiffness values. The stiffness value is therefore an additional tuning parameter rather than a replacement for the other control parameters. The stiffness values are also not made available to the user, so the user cannot set up the system using a stiffness value.

Another use of stiffness in control of a material specimen is in determining the 'stress rate' of a metal specimen. In this case, stiffness is calculated internally in the software from knowledge of the Young's modulus for the material and specimen geometry. This use of stiffness is in order to set a rate of change of position command, but does not affect the feedback control gains, which have already been set.

The present invention provides a method and apparatus whereby all necessary feedback control gains for controlling specimen position or specimen load are calculated from a single adjustable parameter value.

The single adjustable parameter value may be either manually input into the machine, or alternatively calculated from a single physically measurable parameter of the combination of machine and specimen under test.

As a refinement of the above arrangement when performing 'strain' control, it is possible to define an additional measurable parameter to describe the effect of using an extensometer on a localized part of the specimen.

In use, the user simply inputs a single adjustable parameter value into the machine indicative of a characteristic of the specimen to be tested. The machine then makes a computation based on the input value as well as other parameter values and estimates the initial gain settings required by the particular test which the machine is to undertake on the test specimen. The test is then carried out under normal feedback control.

Figure 2:
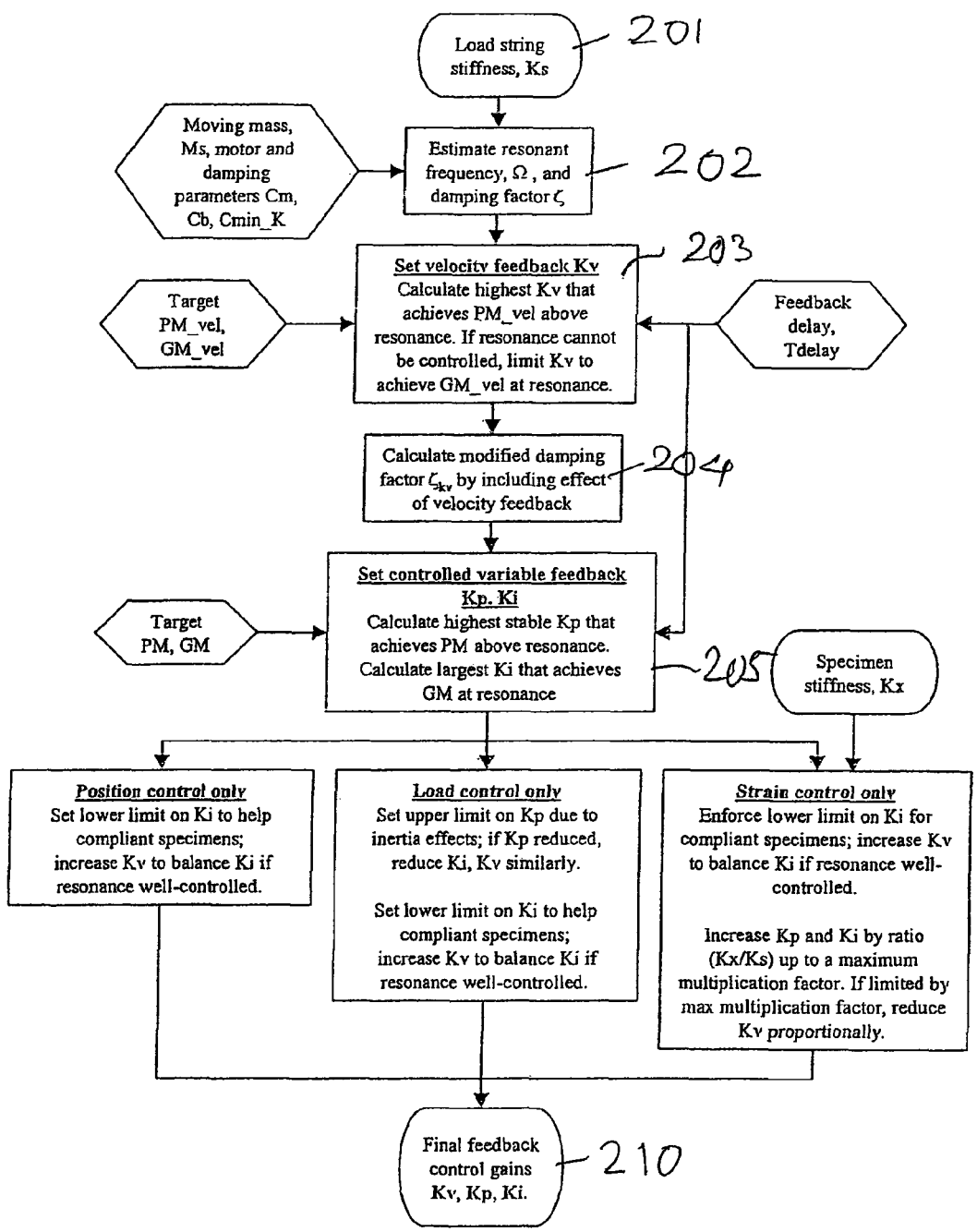

In order that the present invention be more readily understood, an embodiment thereof will now be described with reference to the accompanying drawings, in which:

FIG. 1 shows a diagrammatic representation of a materials testing machine according to the present invention; and FIG. 2 shows a flow chart indicative of the tuning process.

The present invention has been developed on a new type of materials testing machine using a linear electric motor as the actuator, but it is generally applicable to machines using other actuation technologies as long as some measurable characteristics of the actuator utilised are known.

Referring now to FIG. 1, a materials testing machine is shown and comprises a stiff frame 10 comprising a base 11 and a crosshead 12 which holds the drive assembly for an actuator 14. The actuator comprises a piston and cylinder device which in this case is formed by a linear electric motor where the armature constitutes the piston of the actuator. The piston is mounted in bearings 16 and is attached to a specimen grip 18 via a load cell 20. A further specimen grip 21 is attached to the base 11 of the machine and the specimen to be tested is held between the grips 18 and 21.

The position of the piston of the actuator is monitored in some suitable manner for example by an LVDT or a digital encoder and the specimen is monitored in some convenient but known manner e.g. by using the load cell 20 to measure force on the specimen or by using an extensometer 22 which will measure local extension of the specimen under test.

Such a machine is capable of conducting any one of a number of different tests on the specimen and this is achieved by means of suitable controls which drive the actuator. Customarily, these controls are computer operated with the type of test being entered by a user into the machine using some suitable interface system such as a keypad. The control system and data input means are not shown in the drawing.

As has been explained previously, the attachment of the actuator of the machine to a specimen under test having a given stiffness, creates a dynamic system that can be modelled as a force that is a applied to a moving mass attached to a stiffness. The attachment of the moving mass to the stiffness of the specimen creates a resonant mechanical system with a certain natural frequency. The effect of stiffness may depend on other measurable characteristics of the system e.g. the stiffness of the oil column in a hydraulically actuated machine. Further, controlling this resonance is the main challenge of the control system, since there may be very little natural damping in the system and this lack of natural damping is one of the problems associated with utilising a linear electric motor as the actuator. Using feedback control with this resonant system can create an unstable system if control parameters are chosen badly in respect of the amount of feedback which might be present. Additionally, the response of the controller plus actuator limits the usable frequency range in which control is effective. The response of the controller plus actuator is also a complicated function.

With these problems in mind, an algorithm has been derived whereby for position or load control, the only parameter which needs to be set by the user is the load string stiffness Ks which is defined by the change in measured load divided by the change in measured position when a load is applied to the specimen. The specimen stiffness Kx is a more precise value of local stiffness that is used for fine adjustment of the gains when performing strain control with an extensometer. Kx is defined as the change in measured load divided by the change in measured displacement within the contact points of the extensometer. If Kx is not known, setting Ks=Kx is a good first approximation for most specimens and means that if necessary only one parameter is required for strain control tuning as well.

As stated previously, detailed design and implementation has taken place in a machine with a three-phase linear electric motor as the actuator of the machine. The control output is a voltage which is fed to a current amplifier. The current amplifier produces a current proportional to the voltage and the motor force is proportional to the current. The following table describes relevant parameters for the tuning algorithm. Only the stiffness value (s) needs to be adjusted for a given specimen.

| Parameter name | Units | Description | Source |
| --- | --- | --- | --- |
| Ks | N/m | Load string stiffness [stiffness measured of specimen in parallel with frame and fixtures] | Estimated using automatic procedure or entered by user |
| Kx | N/m | Specimen stiffness [stiffness measured of that part of the specimen within an 'extensometer'] | Estimated using automatic procedure or entered by user. If not known, set Kx = Ks. |
| Ms | kg | moving mass | factory-set |
| Cmin_K | s | Minimum expected specimen damping per unit stiffness | factory-set |
| Cm | N | motor constant, the largest force that the motor can produce | factory-set |
| Cb | $m^{-1}s$ | damping parameter for motor, such that Cb * Cm is damping coefficient | factory-set |
| Tdelay | s | delay in feedback control loop | factory-set |
| PM_vel | rad | target phase margin, velocity feedback | factory-set |
| GM_vel | n/a | target gain margin, velocity feedback | factory-set |
| PM | rad | target phase margin, feedback of controlled variable (position, load or strain) | factory-set |
| GM | n/a | target gain margin, feedback of controlled variable (position, load or strain) | factory-set |

The stiffness of the specimen (termed 'load string stiffness', 'Ks') is estimated automatically or entered by the user. The moving mass in the actuator and any other relevant stiffness/compliance is known from the machine specification, hence the natural ('resonant') frequency can be estimated. The 'damping factor' associated with the natural frequency is estimated from other known actuator characteristics and estimated material damping.

The negative effect of the resonance is reduced as much as possible using 'velocity feedback' to add damping to the system. Velocity feedback attempts to simulate 'viscous' damping as closely as possible, but the effect is similar to the use of the D term in a PID controller. The velocity signal is estimated from a digital encoder. The value of velocity feedback gain ('Kv') is chosen to be the largest value that achieves specified 'Phase and Gain Margins' (both well-used concepts in classical control theory), given the knowledge about the resonance and delay in the controller/actuator. A new modified damping factor is calculated to take account of the velocity feedback added.

The proportional feedback gain ('Kp') for the controlled variable (position, load or strain), is calculated using knowledge of the resonance and modified damping factor. Kp is chosen to be the largest value that achieves a specified 'Phase Margin' around the resonant frequency.

The integral feedback gain ('Ki') for the controlled variable (position, load or strain), is calculated using knowledge of the resonance and modified damping factor. Ki is chosen to be the largest value that achieves a specified 'Gain Margin' around the resonant frequency.

Finally, some specific modifications are made to the values of Kv, Kp and Ki, depending on the variable to be controlled. In the case of 'strain control', a second stiffness value ('Kx') is used, which is needed to show the physical relationship between applied force and local displacement where strain is to be measured. If Kx is not available, setting Kx=Ks gives adequate control performance.

Turning now to FIG. 2, this shows in more detail the process carried out by the algorithm in order to set the control gains prior to a test being carried out by the machine. Block 201 indicates the inputting of data representing the load string stiffness Ks into the machine, which as previously described may be entered manually or estimated using an additional procedure. Initially, the algorithm estimates the resonant frequency Ω and damping ζ of the machine system on the basis of the factory settings of the moving mass Ms of the motor and damping parameters Cm, Cb, C min K as represented by block 202. Thereafter, as indicated at block 203, and on the basis of the target phase margin velocity feedback coefficient PMvel and gain margin velocity feedback coefficient GMvel the velocity feedback Kv is calculated such that the highest Kv that achieves PMvel above resonance is provided. However, if resonance cannot be controlled, Kv is limited to achieve the desired gain margin at resonance.

Once the velocity feedback Kv has been set, modified damping factor çkv is calculated in block 204 in order to include the effect of velocity feedback on the system. With this new damping factor, the variable feedback parameters Kp and Ki are calculated in block 205 in order to achieve the highest stable Kp that achieves the target phase margin above resonance and also the largest Ki that achieves gain margin at resonance based on the target phase and gain margins.

Once these steps have been completed, the final feedback control gains Kv, Kp and Ki are set as indicated at block 210 depending on which type of test is to be undertaken by the machine. When only strain is being tested, the system enforces a lower limit on Ki for compliant specimens and increases Kv to balance Ki so that the resonance is well controlled. Depending on the system parameters, Kp and Ki can be increased by the ratio Kx/Ks up to a maximum multiplication factor. If limited by the multiplication factor, it may be necessary to reduce Kv proportionally.

If only position control of the machine is required by the test, then the system sets a lower limit on Ki to help compliant specimens. Kv is increased to balance Ki if the resonance is well controlled in the system.

If only load control is required by the test, then the system sets an upper limit on Kp to limit negative influences on the control due to inertia effects. If Kp is reduced, it is necessary to reduce Ki and Kv similarly. With compliant specimens, a lower limit is set on Ki but it is possible to increase Kv to balance Ki if the resonance is well controlled in the system.

The delay in the feedback control loop, Tdelay, is known in advance and used in the calculations in blocks 203 and 205.

A system designed as described has feedback control gains that are very well suited to the specimen, as long as the specimen characteristics, in particular specimen stiffness, remain the same. In reality, this cannot be guaranteed and it is necessary to detect a sudden change in specimen characteristics as soon as possible, since the feedback control gains may no longer be suitable for the changed specimen characteristics. One way to do this is to estimate specimen stiffness continuously, which has been done previously under the description 'adaptive control'. This method has the advantage of continuously updating the feedback control gains, but as implemented so far is only designed to adapt to a limited range of stiffness variation about an initial value, and requires a number of sequential measurements to calculate a new stiffness estimate, causing significant delay. This is particularly important in the current implementation using an electric linear motor, because of the highly dynamic nature of the actuator. This invention has instead introduced a simple but effective means for detecting a significant specimen change, based on an estimate of acceleration of the actuator. High actuator accelerations can occur either when the specimen stiffness decreases suddenly (for example, the specimen yields or breaks) or when it increases suddenly, and thereby causes a high frequency oscillation. If an acceleration above a preset level is detected, a special set of feedback control gains is used that has been shown to be stable for all expected specimens. The user is informed of this change, which will normally cause the test to end. The measure of acceleration used could be from an accelerometer fitted to the actuator. However, in this implementation it is derived from a digital encoder signal, by numerically differentiating this signal. This implementation has the advantage of a minimum of delay, since the digital encoder signal is free of the random electrical noise associated with typical accelerometer signals, and therefore does not require any further filtering.

While the above description of the invention has been given on the basis of using an electrical actuator/ram with electronic control, it is possible to fit the electronic control arrangement with or without the acceleration monitoring arrangement to other devices using other actuation technologies such as screw drives and hydraulic actuators.

From the above description, it will be apparent that the present invention introduces a simple method of tuning for the user or materials testing machine based only on the stiffness of the specimen under test. This greatly simplifies the process of tuning, provides transparency to the user, and minimises the number of set-up parameters which need to be recorded.

The invention claimed is:

1. A method of operating a material testing machine for testing a specimen, the machine having an electrically controllable actuator arranged to apply a force to the specimen, the method comprising the steps of:
   inputting one and only one adjustable parameter value, wherein the one and only one adjustable parameter value relates to stiffness of the specimen;
   calculating all necessary feedback control gains from the one and only one adjustable parameter value, and subsequently conducting a test of the specimen;
   wherein the actuator is an electrical linear motor arrangement.

2. A method according to claim 1 comprising detecting a sudden change in specimen characteristics by comparing an estimate of actuator acceleration to a preset threshold value and setting the feedback control gains to predetermined values.

3. A method according to claim 2, where the estimate of acceleration comes from numerical differentiation of the signal from a digital encoder that measures actuator displacement.

4. A method according to claim 1 wherein the one and only one adjustable parameter value is manually input via a user interface.

5. A materials testing machine comprising a gripper for engagement with a specimen to be tested, an actuator for controlling movement of the gripper, and a control system including a feedback control arrangement for controlling a parameter of the actuator, wherein the control system includes means for setting the initial gain of the feedback control arrangement from one and only one adjustable parameter value, wherein the one and only one adjustable parameter value relates to stiffness of the specimen and wherein the actuator is an electrical linear motor arrangement.

6. A machine according to claim 5 and comprising a user interface for manually entering the one and only one adjustable parameter value.

7. A machine according to claim 5, and comprising means for monitoring the actuator acceleration and means for setting the feedback control gains to predetermined values in the event that the monitored acceleration exceeds a preset threshold value.

* * * * *